United States Patent
Hategan et al.

(10) Patent No.: US 9,765,010 B2
(45) Date of Patent: Sep. 19, 2017

(54) BRANCHED SATURATED HYDROCARBONS DERIVED FROM OLEFINS

(71) Applicant: Elevance Renewable Sciences, Inc., Woodridge, IL (US)

(72) Inventors: Georgeta Hategan, Woodridge, IL (US); Alexander D. Ilseman, Woodridge, IL (US); Ryan Littich, Woodridge, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 64 days.

(21) Appl. No.: 15/002,311

(22) Filed: Jan. 20, 2016

(65) Prior Publication Data

US 2016/0214923 A1    Jul. 28, 2016

Related U.S. Application Data

(60) Provisional application No. 62/108,684, filed on Jan. 28, 2015.

(51) Int. Cl.
| | |
|---|---|
| *C07C 1/213* | (2006.01) |
| *C07C 5/23* | (2006.01) |
| *C07C 6/04* | (2006.01) |
| *C07C 5/03* | (2006.01) |
| *C07C 67/333* | (2006.01) |
| *C07C 5/27* | (2006.01) |
| *A61K 8/31* | (2006.01) |
| *C11C 3/00* | (2006.01) |
| *C10M 103/00* | (2006.01) |
| *C10M 177/00* | (2006.01) |
| *C10M 105/04* | (2006.01) |

(52) U.S. Cl.
CPC .............. *C07C 67/333* (2013.01); *A61K 8/31* (2013.01); *C07C 5/03* (2013.01); *C07C 5/2775* (2013.01); *C07C 6/04* (2013.01); *C10M 3/00* (2013.01); *C10M 105/04* (2013.01); *C10M 177/00* (2013.01); *C11C 3/00* (2013.01); *C07C 2529/70* (2013.01); *C10M 2203/0206* (2013.01); *C10M 2203/1025* (2013.01); *C10N 2270/00* (2013.01)

(58) Field of Classification Search
CPC .. C07C 1/213; C07C 5/23; C07C 6/04; C07C 5/03
USPC ....... 585/240, 242, 324, 310, 254, 643, 639, 585/664
See application file for complete search history.

(56) References Cited

U.S. PATENT DOCUMENTS

| | | |
|---|---|---|
| 4,545,941 A | 10/1985 | Rosenburg |
| 2011/0237850 A1 | 9/2011 | Luetkens, Jr. et al. |
| 2012/0197031 A1 | 8/2012 | Firth et al. |
| 2013/0130336 A1 | 5/2013 | Olson |

FOREIGN PATENT DOCUMENTS

JP    2526268 B2    8/1996

*Primary Examiner* — Thuan D Dang
(74) *Attorney, Agent, or Firm* — Kilpatrick Townsend & Stockton LLP

(57) ABSTRACT

Methods of making branched isoparaffin compositions derived from natural oil based linear internal olefins are disclosed. Uses of branched isoparaffins formed by such methods are also disclosed.

11 Claims, 1 Drawing Sheet

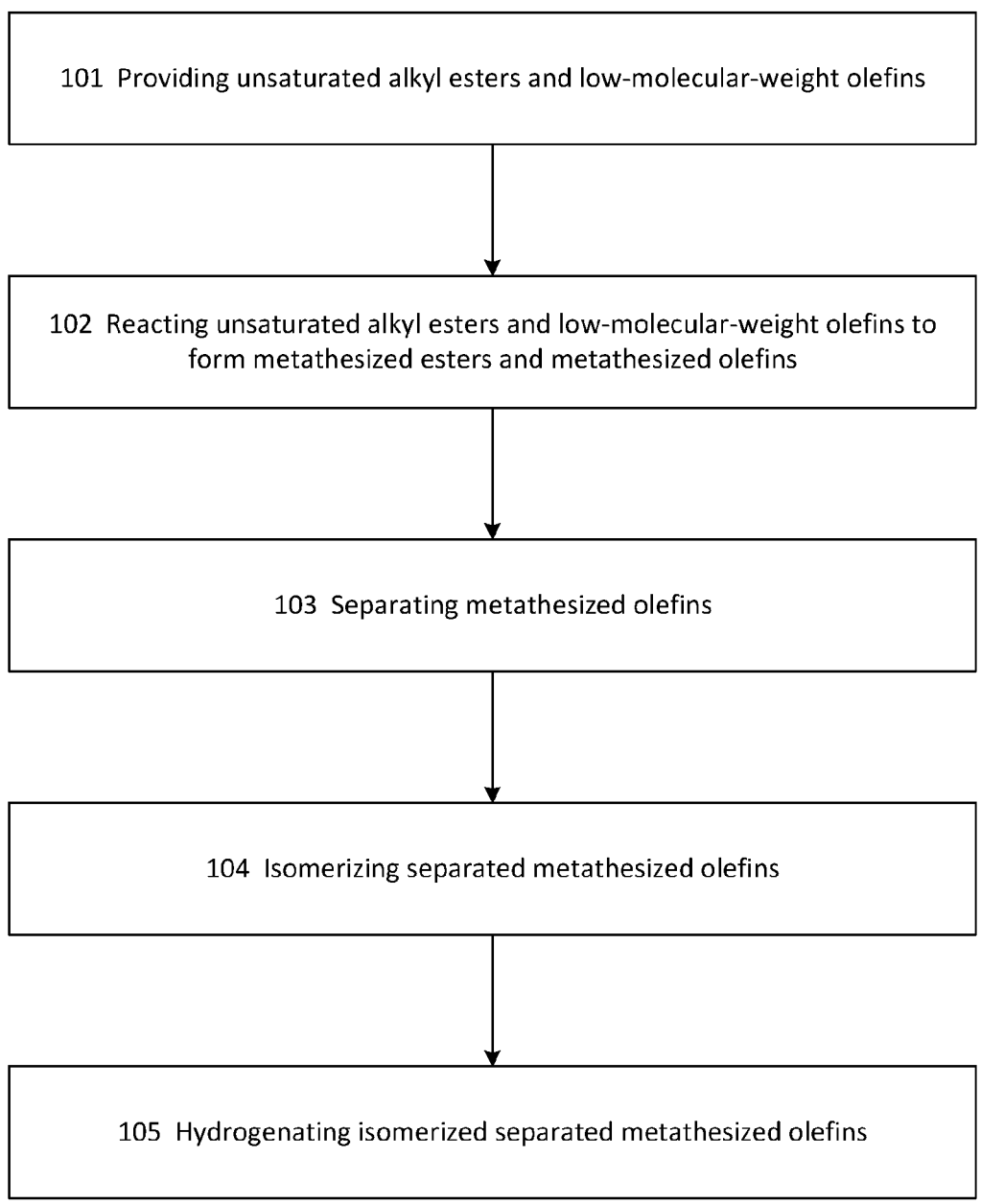

BRANCHED SATURATED HYDROCARBONS DERIVED FROM OLEFINS

CROSS-REFERENCE TO RELATED APPLICATIONS

This application claims the benefit of priority of U.S. Provisional Application No. 62/108,684, filed Jan. 28, 2015, which is hereby incorporated by reference as though fully set forth herein in its entirety.

TECHNICAL FIELD

This application relates to branched isoparaffin compositions derived from natural oil based linear internal olefins.

DESCRIPTION OF RELATED ART

As a result of recent regulatory changes, ecological concerns are intensifying and consumer perception of safety is becoming more important. In many personal care applications, there have been recent concerns regarding the safety of using silicone fluids on the skin. In particular, there have been safety concerns over cyclomethicone, which refers to a family of cyclic dimethyl siloxanes including cyclopentasiloxane (also called D5 or decamethylcyclopentasiloxane), used in personal care applications. As D5 is now also coming under further scrutiny due to its volatility, many formulators are being proactive and looking for a substitute product now, such as a silicone-free product, in the event D5 is to be removed from formulations.

Isoparaffins are branched chain hydrocarbons which are effective surrogates for volatile cyclomethicone. In personal care applications, isoparaffins have a lesser spreading factor on skin and less oily feeling, and hence, have favorable sensory properties. They are attractive for their improved properties over linear paraffins. Other common isoparaffins that may be found in cosmetics and personal care products include: C7-8 isoparaffin, C8-9 isoparaffin, C9-11 isoparaffin, C9-12 isoparaffin, C9-13 isoparaffin, C9-14 isoparaffin, C9-16 Isoparaffin, C10-11 isoparaffin, C10-12 isoparaffin, C10-13 isoparaffin, C11-12 isoparaffin, C11-13 isoparaffin, C11-14 isoparaffin, C12-14 isoparaffin, C12-20 isoparaffin, C13-16 isoparaffin, C18-70 isoparaffin, C20-40 isoparaffin, isooctane and isoeicosane. Long carbon chain isoparaffins (ex. C18 or higher) overcome solubility issues (high solubility at lower temperature) and low temperature properties, gives formulation flexibility and improve sensory properties (occlusiveness, spreadability). Current isoparaffins used in personal care applications are often petroleum based, such as isododecane and isohexadecane. Isododecane is a specialty oligomer from isobutene, which contains a mixture of highly branched C12 isoparaffins and mainly the 2,2,4,6,6-pentamethylheptane isomer. Highly branched hydrocarbon have low biodegradation rates.

Therefore, there is a continuing need to develop hydrocarbon compositions, and methods of making such compositions, that are highly branched and have a high bio-content.

SUMMARY

The present disclosure generally provides olefins or mixture of olefins can be isomerized and hydrogenated by using known procedures to give a high bio-content isoparaffins, with lower degree of branching.

In at least one aspect, the disclosure provides methods of forming an isoparaffin composition, the method comprising: providing (a) unsaturated alkyl esters and (b) low-molecular-weight olefins; reacting the unsaturated alkyl esters and the low-molecular-weight olefins in the presence of a metathesis catalyst to form a metathesis product comprising metathesized esters and metathesized olefins, wherein the metathesized olefins comprise one or more linear internal olefins; separating at least a portion of the metathesized olefins from the metathesis product to form a separated olefin composition, wherein the separated olefin composition comprises one or more linear internal olefins; isomerizing the one or more linear internal olefins comprised by the separated separated olefin composition to form a isomerized olefin composition, wherein the isomerized olefin composition comprises one or more branched olefins; and hydrogenating the one or more branched olefins comprised by the isomerized olefin composition to form an isoparaffin composition.

In a second aspect, the disclosure provides personal care compositions comprising an isoparaffin composition formed by the methods of the first aspect.

Further aspects and embodiments are set forth in the Detailed Description of the present disclosure.

BRIEF DESCRIPTION OF THE DRAWINGS

FIG. 1 depicts a method of making an isoparaffin composition according to certain embodiments disclosed herein.

DETAILED DESCRIPTION

It is to be understood that unless specifically stated otherwise, references to "a," "an," and/or "the" may include one or more than one, and that reference to an item in the singular may also include the item in the plural.

The term "natural oil" refers to oils or fats derived from plants or animals. The term "natural oil" includes natural oil derivatives, unless otherwise indicated, and such natural oil derivatives may include one or more natural oil derived unsaturated carboxylic acids or derivatives thereof. The natural oils may include vegetable oils, algae oils, fungus oils, animal oils or fats, tall oils, derivatives of these oils, combinations of two or more of these oils, and the like. The natural oils may include, for example, canola oil, rapeseed oil, coconut oil, corn oil, cottonseed oil, olive oil, palm oil, peanut oil, safflower oil, sesame oil, soybean oil, sunflower seed oil, linseed oil, palm kernel oil, tung oil, jatropha oil, mustard oil, camellina oil, pennycress oil, castor oil, coriander oil, almond oil, wheat germ oil, bone oil, lard, algal oil, tallow, poultry fat, yellow grease, fish oil, mixtures of two or more thereof, and the like. The natural oil (e.g., soybean oil) may be refined, bleached and/or deodorized. The natural oil may comprise a refined, bleached and/or deodorized natural oil, for example, a refined, bleached, and/or deodorized soybean oil (i.e., RBD soybean oil). The natural oil may also comprise a tall oil or an algal oil.

Natural oils of the type described herein typically are composed of triglycerides of fatty acids. These fatty acids may be either saturated, monounsaturated or polyunsaturated and contain varying chain lengths ranging from $C_6$ to $C_{30}$. These fatty acids may also be mono, di-, tri-, or poly-carboxylic acids. In some embodiments, the fatty acids may include hydroxy-substituted variants, aliphatic, cyclic, alicyclic, aromatic, branched, aliphatic- and alicyclic-substituted aromatic, aromatic-substituted aliphatic and alicyclic groups, saturated and unsaturated variants, and heteroatom substituted variants thereof. Some common fatty acids include saturated fatty acids such as lauric acid (dodecanoic acid), myristic acid (tetradecanoic acid), palmitic acid (hexadecanoic acid), stearic acid (octadecanoic acid), arachidic acid (eicosanoic acid), and lignoceric acid (tetracosanoic acid); unsaturated fatty acids as decenoic acid, undecenoic acid, dodecenoic acid, palmitoleic (a C16 acid), and oleic acid (a C18 acid); polyunsaturated acids include such fatty acids as linoleic acid (a di-unsaturated C18 acid), linolenic acid (a tri-unsaturated C18 acid), and arachidonic acid (a tetra-unsubstituted C20 acid).

The natural oils are further comprised of esters of these fatty acids in random placement onto the three sites of the trifunctional glycerine molecule. Such esters may be mono- or di-esters or poly-esters of these acids thereof. Different natural oils will have different ratios of these fatty acids, and within a given natural oil there is a range of these acids as well depending on such factors as where a vegetable or crop is grown, maturity of the vegetable or crop, the weather during the growing season, etc. Thus, it is difficult to have a specific or unique structure for any given natural oil, but rather a structure is typically based on some statistical average. For example soybean oil contains a mixture of stearic acid, oleic acid, linoleic acid, and linolenic acid in the ratio of 15:24:50:11, and an average number of double bonds of 4.4-4.7 per triglyceride. One method of quantifying the number of double bonds is the iodine value (IV) which is defined as the number of grams of iodine that will react with 100 grams of vegetable oil. Therefore for soybean oil, the average iodine value range is from 120-140. Soybean oil may comprises about 95% by weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated carboxylic acids, as a non-limiting example, oleic acid (9-octadecenoic acid), linoleic acid (9, 12-octadecadienoic acid), and linolenic acid (9,12,15-octadecatrienoic acid).

The term "linear internal olefin" may refer to an olefin whose double bond in located anywhere along the carbon chain except at a terminal carbon atom. The linear internal olefin does not have any alkyl, aryl, or alicyclic branching on any of the double bond carbon atoms or on any carbon atoms adjacent to the double bond carbon atoms. The linear internal olefin may have between 2 and 40 carbons in its hydrocarbon chain. In some embodiments, the linear internal olefin has between 10 and 18 carbons in its hydrocarbon chain.

As used herein, the terms "metathesize" and "metathesizing" may refer to the reacting of a natural oil feedstock in the presence of a metathesis catalyst to form a metathesized natural oil product comprising a new olefinic compound and/or esters. Metathesizing may refer to cross-metathesis (a.k.a. co-metathesis), self-metathesis, ring-opening metathesis, ring-opening metathesis polymerizations ("ROMP"), ring-closing metathesis ("RCM"), and acyclic diene metathesis ("ADMET"). As a non-limiting example, metathesizing may refer to reacting two triglycerides present in a natural feedstock (self-metathesis) in the presence of a metathesis catalyst, wherein each triglyceride has an unsaturated carbon-carbon double bond, thereby forming an oligomer having a new mixture of olefins and esters that may comprise one or more of: metathesis monomers, metathesis dimers, metathesis trimers, metathesis tetramers, metathesis pentamers, and higher order metathesis oligomers (e.g., metathesis hexamers, metathesis heptamers, metathesis octamers, metathesis nonamers, metathesis decamers, and higher than metathesis decamers and above). In some aspects, a metathesis dimer refers to a compound formed when two unsaturated polyol ester molecules are covalently bonded to one another by a self-metathesis reaction, and a metathesis trimer refers to a compound formed when three unsaturated polyol ester molecules are covalently bonded together by metathesis reactions. In some aspects, a metathesis trimer is formed by the cross-metathesis of a metathesis dimer with an unsaturated polyol ester. In some aspects, a metathesis tetramer refers to a compound formed when four unsaturated polyol ester molecules are covalently bonded together by metathesis reactions. In some aspects, a metathesis tetramer is formed by the cross-metathesis of a metathesis trimer with an unsaturated polyol ester. Metathesis tetramers also may be formed, for example, by the cross-metathesis of two metathesis dimers. Higher unit metathesis products also may be formed. For example, metathesis pentamers and metathesis hexamers also may be formed. In some embodiments, metathesis reactions are commonly accompanied by isomerization, which may or may not be desirable. See, for example, G. Djigoué and M. Meier, *Appl. Catal., A* 346 (2009) 158, especially FIG. 3. Thus, the skilled person might modify the reaction conditions to control the degree of isomerization or alter the proportion of cis- and trans-isomers generated. For instance, heating a metathesis product in the presence of an inactivated metathesis catalyst might allow the skilled person to induce double bond migration to give a lower proportion of product having trans-$\Delta^9$ geometry.

The term "metathesis catalyst" includes any catalyst or catalyst system that catalyzes a metathesis reaction. Any known metathesis catalyst may be used, alone or in combination with one or more additional catalysts. Suitable homogeneous metathesis catalysts include combinations of a transition metal halide or oxo-halide (e.g., $WOCl_4$ or $WCl_6$) with an alkylating cocatalyst (e.g., $Me_4Sn$), or alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

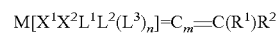

$$M[X^1X^2L^1L^2(L^3)_n]=C_m=C(R^1)R^2$$

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086, the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is part of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ-with respect to the carbene carbon to provide the bidentate ligand. Examples of suitable Grubbs-Hoveyda catalysts appear in the '086 publication.

The structures below provide just a few illustrations of suitable catalysts that may be used:

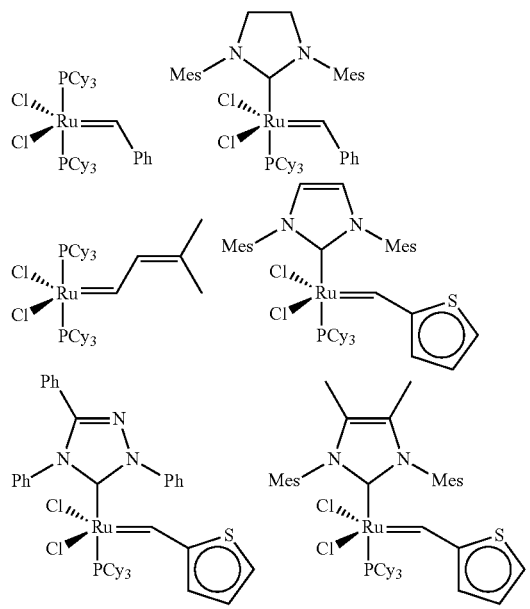

Heterogeneous catalysts suitable for use in the self- or cross-metathesis reaction include certain rhenium and molybdenum compounds as described, e.g., by J. C. Mol in *Green Chem.* 4 (2002) 5 at pp. 11-12. Particular examples are catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins.

For additional examples of suitable catalysts for self- or cross-metathesis, see U.S. Pat. Nos. 4,545,941, 5,312,940, 5,342,909, 5,710,298, 5,728,785, 5,728,917, 5,750,815, 5,831,108, 5,922,863, 6,306,988, 6,414,097, 6,696,597, 6,794,534, 7,102,047, 7,378,528, and U.S. Pat. Appl. Publ. No. 2009/0264672 A1, and PCT/US2008/009635, pp. 18-47, all of which are incorporated herein by reference. A number of metathesis catalysts that may be advantageously employed in metathesis reactions are manufactured and sold by Materia, Inc. (Pasadena, Calif.).

Method for Making Isoparaffins from Linear Internal Olefins.

The method for generating isoparaffins is by reacting a linear internal olefin with an appropriate isomerization catalyst to from an isomerized branched chain olefin mixture, whereby the isomerized branched chain olefin mixture is hydrogenated to produce the isoparaffins.

Such linear internal olefins are produced via cross-metathesizing of unsaturated alkyl esters with low molecular weight olefins, which generates the new linear internal olefins and new unsaturated alkyl esters that can have reduced chain length. In some embodiments, the linear internal olefins are produced via self-metathesizing of low molecular weight olefins, such as linear alpha olefins. For example, if one linear alpha-olefin having n carbon atoms is subjected to self-metathesis, then the product formed will be a linear internal olefin having (2n−2) carbon atoms with the double bond at the center position, i.e., after carbon atom n−1. In some embodiments, the linear internal olefins are produced via cross-metathesis of low molecular weight olefins, such as linear alpha olefins. If a mixture of several linear alpha-olefins is subjected to cross-metathesis, then several linear internal olefin products are formed, all of which will have the double bond at an internal position. For example, if the shortest alpha-olefin fed to metathesis has 4 carbons, then the internal olefins formed from metathesis will have the double bond at least after or even more internal than the third carbon atom.

The unsaturated alkyl esters utilized in the cross metathesis may be generated as follows. After an optional treatment of the natural oil feedstock (which may include thermal and/or chemical, and/or adsorbent methods to remove catalyst poisons, or a partial hydrogenation treatment to modify the natural oil feedstock's reactivity with the metathesis catalyst), the natural oil is reacted with itself, or combined with a low-molecular-weight olefin in a metathesis reactor in the presence of a metathesis catalyst. In certain embodiments, in the presence of a metathesis catalyst, the natural oil undergoes a self-metathesis reaction with itself. In other embodiments, in the presence of the metathesis catalyst, the natural oil undergoes a cross-metathesis reaction with a low-molecular-weight olefin. In certain embodiments, the natural oil undergoes both self- and cross-metathesis reactions in parallel metathesis reactors. Multiple, parallel, or sequential metathesis reactions (at least one or more times) may be conducted. The self-metathesis and/or cross-metathesis reaction form a metathesized natural oil product wherein the metathesized natural oil product comprises olefins (including linear internal olefins) and unsaturated alkyl esters.

In some embodiments, the unsaturated alkyl esters refer to a compound that has an alkene chain with a terminal ester group. The alkene chain may be linear or branched, and may optionally include one or more functional groups in addition to the ester group. For example, some unsaturated alkyl esters include one or more hydroxyl groups in addition to the ester group. Unsaturated alkyl esters include unsaturated monoesters and unsaturated polyol esters. Unsaturated monoesters have an alkene chain that terminates in an ester group, for example, an alkyl ester group such as a methyl ester. The alkene chain of the unsaturated alkyl esters typically contains about 4 to about 30 carbon atoms, more typically about 4 to 22 carbon atoms. The unsaturated alkyl esters have at least one carbon-carbon double bond in the alkene chain and may have more than one double bond in the alkene chain. In some embodiments, the unsaturated alkyl esters may comprise dibasic esters, including, but not limited to, 9-ODDAME (9-octadecenoic diacid methyl ester).

The low molecular weight olefins used in either the cross metathesis or self metathesis may be derived from one or more of the following: (1) a natural oil feedstock, (2) a fatty alcohol which is dehydrated, (3) a sugar fermentation derived alcohol which is dehydrated, (4) a biological process that selectively produced olefins from naturally occurring saturated hydrocarbon compounds, and (5) ethanol. In other aspects, the low molecular weight olefins are derived from free fatty esters, wherein the free fatty esters are reduced to form a terminal alcohol, which is then catalytically dehydrated to form the low molecular weight olefins.

The low molecular weight olefins may refer to any unsaturated linear, branched, or cyclic olefins in the C2 to C18 range. The low molecular weight olefins may include alpha-olefins or terminal olefins, wherein the unsaturated carbon-carbon bond is present at one end of the compound, and which may be represented by the general formula of $CH_2=CH-R^x$ where $-R^x$ is an organic group. The low molecular weight olefins may also include polyunsaturated olefins (e.g., dienes and trienes). The low molecular weight olefins may also include internal olefins. For example, the internal olefin may have the structure: $R^1R^2C=CR^3R^4$ where $R^1$, $R^2$, $R^3$, and $R^4$ are each, independently, hydrogen or an organic group, with the proviso that at least one of $R^1$ or $R^2$ is an organic group, and at least one of $R^3$ or $R^4$ is an organic group. Useful internal olefins may be symmetric or asymmetric. As used herein, the organic group may be an aliphatic group, an alicyclic group or an aromatic group. Organic groups may optionally include heteroatoms (e.g., O, N, P or S atoms), as well as functional groups (e.g., carbonyl groups). The term aliphatic group means a saturated or unsaturated, linear or branched, hydrocarbon group. This term is used to encompass alkyl groups. The term alkyl group means a monovalent, saturated, linear, branched, or cyclic hydrocarbon group. An alicyclic group is an aliphatic group arranged in one or more closed ring structures. The term is used to encompass saturated (i.e., cycloparaffins) or unsaturated (cycloolefins or cycloacetylenes) groups. An aromatic or aryl group is an unsaturated cyclic hydrocarbon having a conjugated ring structure. Included within aromatic or aryl groups are those possessing both an aromatic ring structure and an aliphatic or alicyclic group.

Non-limiting examples of low molecular weight olefins includes ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, cyclohexene, 1,4-heptadiene, 1-heptene, 3,6-nonadiene, 3-nonene, 1,4,7-octatriene, styrene, vinyl cyclohexane, cardanol, limonene, and isoprene. In certain embodiments, it is preferable to use a mixture of low molecular weight olefins.

As a non-limiting example, cross-metathesis of unsaturated alkyl esters with low molecular weight olefins generates new linear internal olefins and new unsaturated alkyl esters that can have reduced chain length. For instance, cross-metathesis of methyl oleate and 3-hexene provides 3-dodecene and methyl 9-dodecenoate (see also U.S. Pat. No. 4,545,941). A variety of cross-metathesis reactions involving an α-olefin and an unsaturated alkyl ester (as the internal olefin source) are described. Thus, for example, reaction of soybean oil with propylene followed by hydrolysis gives, among other things, 1-decene, 2-undecenes, 9-decenoic acid, and 9-undecenoic acid. As an additional example, reaction of meadowfoam seed oil with propylene gives, among other things, 1-hexadecene, 2-hexadecenes and 5-hexenoic acid. Another non-limiting example is the cross metathesis of methyl oleate with ethylene, which will yield cross-metathesis products of 1-decene and methyl-9-decenoate. Another non-limiting example is the self-metathesis of linear alpha olefins, such as the self-metathesis of 1-decene to 9-octadecene, or the self-metathesis of 1-nonene to 8-hexadecene. Another non-limiting example is the cross-metathesis of linear alpha olefins, where 5-hexadecene would be prepared from cross metathesis of 1-hexene with 1-dodecene, or where 4-hexadecene would be prepared from cross metathesis of 1-pentene with 1-tridecene, or where 7-hexadecene would be prepared from cross metathesis of 1-octene with 1-decene. In some embodiments, the cross metathesis of 1-decene and 1-dodecene may yield high distributions of 9-octadecene. In some embodiments, the cross metathesis of 1-nonene and 1-decene may yield high distributions of 8-pentadecene.

The targeted linear internal olefin is then reacted with an appropriate isomerization catalyst, to produce an isomerized branched chain olefin mixture. Subsequently, the isomerized branched chain olefin mixture is hydrogenated to produce isoparaffins.

Isomerization is a hydrocarbon transformation reaction, and it can be catalyzed by homogeneous or heterogeneous strong acids. Isomerization catalysts may be Brönsted or Lewis acidic in nature. In isomerization reactions, the molecular formula of one compound does not change, but its structure changes. One type of isomerization is skeletal isomerization. In skeletal isomerization of linear olefins, the linear olefins are converted into branched, tri-substituted or tetra-substituted olefins depending upon the position of the double bond. Preferably, the skeletal isomerization is conducted at elevated temperature in the range from about 200° C. to about 500° C., more preferably from about 250° C. to about 350° C. Preferably, the skeletal isomerization reaction is conducted at a pressure of about 0.1 psi to about 50 psi, and more preferably from about 10 psi to about 20 psi.

Suitable isomerization catalysts include molecular sieves (both aluminosilicate zeolites and silicoaluminophosphates), amorphous aluminosilicates, cationic acidic clays, and other solid acid catalysts. The isomerization catalysts described herein may be supported on a support. For example, the catalysts may be deposited on, contacted with, vaporized with, bonded to, incorporated within, adsorbed or absorbed in, or on, one or more supports or carriers. The catalysts described herein may be used individually or as mixtures. The isomerizations using multiple catalysts may be conducted by addition of the catalysts simultaneously or in a sequence.

According to International Zeolite Association (IZA) definitions, molecular sieves can be categorized according to the size of the pore opening. Examples of the molecular sieves can be of the large (>12-ring pore opening), medium (10-ring opening) or small (<8-ring pore opening) pore type. The molecular sieves structure types can be defined using three letter codes. Non-limiting examples of small pore molecular sieves include AEI, AFT, ANA, APC, ATN, ATT, ATV, AWW, BIK, CAS, CHA, CHI, DAC, DDR, EDI, ERI, GIS, GOO, KFI, LEV, LOV, LTA, MER, MON, PAU, PHI, RHO, ROG, SOD, THO, and substituted forms thereof. Non-limiting examples of medium pore molecular sieves include AFO, AEL, EUO, HEU, FER, MEL, MFI, MTW, MTT, MWW, TON, and substituted forms thereof. Non-limiting examples of large pore molecular sieves include BEA, CFI, CLO, DNO, EMT, FAU, LTL, MOR and substituted forms thereof. Other zeolite catalysts have a Si/Al molar ratio of greater than 2 and at least one dimension of the pore openings greater than or equal to 10-ring. Other solid zeolites include ZSM-5 (MFI), zeolite beta (BEA), USY family zeolites (FAU), MCM-22, MCM-49, MCM-56 (MWW). Mesoporous materials with pore openings greater than 20 angstroms, such as the MCM-41 family and SBA-15 type with aluminum incorporated into the structure and thus possess acidity, can also be used as oligomerization catalysts. Other zeolites may include 720KOA, 640HOA, and 690HOA available from Tosoh Corporation, or CP811C-300, CBV760, CBV901 available from Zeolyst International.

Other examples of clay catalysts include acidic, natural or synthetic Montmorillonites (including K10, KSF, K30), bentonite, silica clay, alumina clay or magnesia clay or silica-alumina clay. Other clay catalysts may include neutral clays (F-100, Ca—Mg bentonite), Fulcat 200, Fulcat 400, and acid treated clays, such as DC-2 (AmCol, acid treated Na—Mg bentonite). Other catalysts for the oligomerization processes may include toluene sulfonic acid catalyst, ion-exchange resin catalyst, and aluminum trichloride catalyst. Commercially available acidic forms of Filtrol clays are also suitable for this oligomerization process. Other solid acid catalysts, such as activated WOx/ZrO$_2$catalysts, other metal oxides, Nafions or other acidic ion-exchanged resins, such as Dowex or Amberlyst cation exchanged are also suitable for the oligomerization reaction.

Upon generation of the isomerized branched olefins, such branched olefins are then hydrogenated to produce isoparaffins. As used herein, isoparaffins are a saturated aliphatic hydrocarbon whose molecules have at least one carbon atom bonded to at least three other carbon atoms or at least one side chain (i.e., a molecule having one or more tertiary or quaternary carbon atoms), and preferably wherein the total number of carbon atoms per molecule is in the range between about 2 and 100, preferably 5 to 50 carbon atoms, and more preferably, 10 to 40 carbon atoms. In some embodiments, the isoparaffins may be blended with various olefins and/or unsaturated alkyl esters, either individually or in combinations thereof.

The hydrogenation may be conducted according to any known method for hydrogenating double bond-containing compounds such as natural oils. Hydrogenation may be carried out in a batch or in a continuous process and may be partial hydrogenation or complete hydrogenation. In a representative batch process, a vacuum is pulled on the headspace of a stirred reaction vessel and the reaction vessel is charged with the material to be hydrogenated. The material is then heated to a desired temperature. Typically, the temperature ranges from about 50° C. to 350° C., for example, about 100° C. to 300° C. or about 150° C. to 250° C. The desired temperature may vary, for example, with hydrogen gas pressure. Typically, a higher gas pressure will require a lower temperature. In a separate container, the hydrogenation catalyst is weighed into a mixing vessel and is slurried in a small amount of the material to be hydrogenated. When the material to be hydrogenated reaches the desired temperature, the slurry of hydrogenation catalyst is added to the reaction vessel. Hydrogen gas is then pumped into the reaction vessel to achieve a desired pressure of H$_2$ gas. Typically, the H$_2$ gas pressure ranges from about 15 to 3000 psig, for example, about 15 psig to 90 psig. As the gas pressure increases, more specialized high-pressure processing equipment may be required. Under these conditions the hydrogenation reaction begins and the temperature is allowed to increase to the desired hydrogenation temperature (e.g., about 120° C. to 200° C.) where it is maintained by cooling the reaction mass, for example, with cooling coils. When the desired degree of hydrogenation is reached, the reaction mass is cooled to the desired filtration temperature.

In some embodiments, the isomerized branched olefin is hydrogenated in the presence of a metal catalyst, typically a transition metal catalyst, for example, nickel, copper, palladium, platinum, molybdenum, iron, ruthenium, osmium, rhodium, or iridium catalyst. Combinations of metals may also be used. Useful catalyst may be heterogeneous or homogeneous. The amount of hydrogenation catalysts is typically selected in view of a number of factors including, for example, the type of hydrogenation catalyst used, the amount of used, the degree of unsaturation in the material to be hydrogenated, the desired rate of hydrogenation, the desired degree of hydrogenation (e.g., as measure by iodine value (IV)), the purity of the reagent, and the H$_2$ gas pressure.

FIG. 1 illustrates certain embodiments of the methods 100 described herein, the method including: providing unsaturated alkyl esters and low-molecular-weight olefins 101; reacting the unsaturated alkyl esters and the low-molecular-weight olefins in the presence of a metathesis catalyst to form a metathesis product comprising metathesized esters and metathesized olefins 102; separating at least a portion of the metathesized olefins from the metathesis product to form a separated olefin composition 103; isomerizing the one or more linear internal olefins comprised by the separated separated olefin composition to form a isomerized olefin composition 104; and hydrogenating the one or more branched olefins comprised by the isomerized olefin composition to form an isoparaffin composition 105.

Uses/Applications for Branched Isoparaffins

The branched isoparaffins, blends, or derivatives therefrom, may be used in various industrial or commercial applications. As used in this context, "derivatives" includes not only chemical compositions or materials resulting from the reaction of branched isoparaffins with at least one other reactant to form a reaction product, but also further downstream reaction products of those reaction products as well.

The end uses for branched isoparaffins, blends or derivatives therefrom, include cosmetics and personal care applications, solid and liquid polyamide resins, epoxy and polyester resins for use, in drug delivery, fuel additives, I&I cleaning applications, leather treatment, in thermographic inks and coatings for plastic films, papers, and paperboard. The branched isoparaffins, blends or derivatives therefrom, may be incorporated into various formulations and used as lubricants, functional fluids, fuels and fuel additives, additives for such lubricants, functional fluids and fuels, plasticizers, asphalt additives, friction reducing agents, antistatic agents in the textile and plastics industries, flotation agents, antifoaming agents, gelling agents, epoxy curing agents, corrosion inhibitors, polishes, leather and vinyl cleaner/protectant, solvents or co-solvents, pigment wetting agents, in cleaning compositions, plastics, coatings, adhesives, surfactants, emulsifiers, skin feel agents, film formers, rheological modifiers, solvents, release agents, conditioners, and dispersants, hydrotropes, etc. Where applicable, such formulations may be used in end-use applications including, but not limited to, personal care, as well as household and industrial and institutional cleaning products, oil field applications, gypsum foamers, coatings, adhesives and sealants, agricultural formulations, to name but a few. Thus, the branched isoparaffins, blends, or derivatives therefrom may be employed as or used in applications including, but not limited to bar soaps, bubble baths, shampoos, conditioners, body washes, facial cleansers, hand soaps/washes, shower gels, wipes, baby cleansing products, creams/lotions, hair treatment products, anti-perspirants/deodorants, enhanced oil recovery compositions, solvent products, gypsum products, gels, semi-solids, detergents, heavy duty liquid detergents (HDL), light duty liquid detergents (LDL), liquid detergent softener antistat formulations, dryer softeners, hard surface cleaners (HSC) for household, autodishes, rinse aids, laundry additives, carpet cleaners, softergents, single rinse fabric softeners, I&I laundry, oven cleaners, car washes, transportation cleaners, drain cleaners, defoamers, anti-foamers, foam boosters, anti-dust/dust repellents, industrial cleaners, institutional cleaners, industrial solvents, janitorial cleaners, glass cleaners, graffiti removers, concrete cleaners, metal/machine parts cleaners, pesticide emulsifiers, agricultural formulations and food service cleaners.

The branched isoparaffins, blends, or derivatives therefrom may be incorporated into, for example, various compositions and used as lubricants, functional fluids, fuels, additives for such lubricants, functional fluids and fuels, plasticizers, asphalt additives and emulsifiers, friction reducing agents, plastics, coatings, adhesives, surfactants, emulsifiers, skin feel agents, film formers, rheological modifiers, biocides, biocide potentiators, solvents, release agents, conditioners, and dispersants, etc. Where applicable, such compositions may be used in end-use applications including, but not limited to, personal care liquid cleansing products, conditioning bars, oral care products, household cleaning products, including liquid and powdered laundry detergents, liquid and sheet fabric softeners, hard and soft surface cleaners, sanitizers and disinfectants, and industrial cleaning products, emulsion polymerization, including processes for the manufacture of latex and for use as surfactants as wetting agents, dispersants, solvents, and in agriculture applications as formulation inerts in pesticide applications or as adjuvants used in conjunction with the delivery of pesticides including agricultural crop protection turf and ornamental, home and garden, and professional applications, and institutional cleaning products. They may also be used in oil field applications, including oil and gas transport, production, stimulation and drilling chemicals and reservoir conformance and enhancement, organoclays for drilling muds, specialty foamers for foam control or dispersancy in the manufacturing process of gypsum, cement wall board, concrete additives and firefighting foams, paints and coatings and coalescing agents, paint thickeners, adhesives, or other applications requiring cold tolerance performance or winterization (e.g., applications requiring cold weather performance without the inclusion of additional volatile components).

The branched isoparaffins, blends, or derivatives therefrom may be used in all types of adhesives, sealants and coatings, tackifiers, solvents, tire and rubber modification for tread and tire enhancement, air care (soy gels, air freshener gels) cutting, drilling and lubricant oils, linoleum binders, paper sizing, clear candles, ink resins and binders, road marking resins, reflective road marking through incorporation of glass beads on road markings, pigment coatings and as an end block reinforcing resin in styrene-isoprene-styrene (SIS) and styrene-butadiene-styrene (SBS) block copolymers for pressure sensitive adhesives.

The formulations mentioned above commonly contain one or more additional components for various purposes, such as surfactants, anionic surfactants, cationic surfactants, ampholtyic surfactants, zwitterionic surfactants, mixtures of surfactants, builders and alkaline agents, enzymes, adjuvants, fatty acids, odor control agents and polymeric suds enhancers, and the like.

The following examples merely illustrate the invention. The skilled person will recognize many variations that are within the spirit of the invention and scope of any current or future claims.

EXAMPLES

Example 1—Skeletal Isomerization of 9-octadecene (600 mL Parr Reactor)

Isomerization Using Acidic Zeolite HSZ-640HOA (Tosoh):

A mixture of 300 g of 9-octadecene and 24 g (8%) catalyst were loaded in a 600 mL Parr reactor, sealed, purged with $N_2$ for 30 minutes, an initial pressure of $N_2$ (10 psi) was applied and the mixture was heated to 250° C. under 600 rpm stirring. The reaction mixture reached the desired temperature and then stirred at this temperature for 4 hours. After 4 hrs, the reaction mixture was cooled to 60° C. and transferred to a flask.

The mixture was vacuum filtered using Buchner funnel (medium pore) and a pad of basic celite. This was the main filtrate. Catalyst was washed with heptane several times to maximize recovery. The second filtrate was concentrated using a rotary evaporator to remove heptane used for catalyst washing. Combined filtrates (280 g, 93.33% mass recovery) was subject to hydrogenation. Crude product composition by GC/FID (area %) after derivatization is: Monomer+other byproducts 90%, Dimer: 10%.

Hydrogenation of Isoparaffin:

The 600 mL Parr reactor was charged with the substrate isoparaffin mixture (320 g) and 2.5 wt % of 10% palladium on carbon with respect to the substrate to be used (8.0 g of catalyst per 320 g of substrate). Next, the vessel was attached to a pressure head, an $N_2$ purge and pressure check is performed, and the vessel was pressurized to 50 psi with $H_2$. The mixture was stirred at 600 rpm, and heated to 100° C. Temperature and hydrogen pressure was raised to a maximum of 150° C. and 200 psi or lower and maintained there until the uptake of hydrogen ceased and/or reached its theoretical amount (about 4 hrs). After the reaction was done, the mixture was filtered through a celite pad and the filtrate (300 g) was fractionated using short path vacuum distillation to remove monomers from dimers. The resulting composition was analyzed by GC/FID and compared to isohexadecane and n-octadecene.

Example 2—Partial Isomerization

Isomerization using acidic zeolite HSZ-640HOA (Tosoh):

A mixture of 300 g of 9-octadecene and 24 g (8%) catalyst were loaded in a 600 mL Parr reactor, sealed, purged with $N^2$ for 30 minutes, an initial pressure of $N^2$ (10 psi) was applied and the mixture was heated to 220° C. under 600 rpm stirring. The reaction mixture reached the desired temperature and then stirred at this temperature for 4 hours. After 4 hrs, the reaction mixture was cooled to 60° C. and transferred to a flask.

The mixture was vacuum filtered using Buchner funnel (medium pore) and a pad of basic celite. This was the main filtrate. Catalyst was washed with heptane several times to maximize recovery. The second filtrate was concentrated using a rotary evaporator to remove heptane used for catalyst washing. Combined filtrates (280 g, 93.33% mass recovery) was subject to hydrogenation. Crude product composition by GC/FID (area %) is: Monomer: 96%, Dimer: 4%.

Analytical Characterization

Analytical studies involving GC, GC/MS and GPC were performed to determine the composition of C18 isoparaffins obtained in 2 steps (isomerization and hydrogenation) from 9-octadecene using different reaction conditions. The material obtained at higher temperature was completely isomerized and have the following composition: <C18 alkanes present at 8.5%, C18 isomers present at 59%, C19-C35 alkanes present at 24% and C36 alkanes present at 9%. The material obtained at lower temperature was less isomerized (60%) and has the following composition: <C18 alkanes present at 0.8%, C18 isomers present at 92%, C19-C35 alkanes present at 2.9% and C36 alkanes present at 4%. GS/MS analysis of material obtained at higher temperature (1162-93) shows the following composition:

TABLE 1

| Summary of Sample Composition | |
|---|---|
| Major Component in Group | Concentration, wt % |
| <C18 Alkanes | 8.5 |
| C18 Isomers + nC18 | 58.8 |
| C19-C35 Alkanes | 23.6 |
| C36 Isomers | 9.1 |

GS/MS analysis of material obtained at lower temperature (1194-28) shows the following composition:

TABLE 2

| Composition of Isomerized Octadecanes. | | |
|---|---|---|
| Component | Concentration, % 1194-28 | Concentration, % 1162-93 |
| <C18 Alkanes | 0.8 | 8.5 |
| C18 Isomers + nC18 | 92.1 | 58.8 |
| C19-C35 Alkanes | 2.9 | 23.6 |
| C36 Isomers | 4.1 | 9.1 |

Experimental

GC/MS data were acquired on an Agilent 7890 coupled to a quadrupole mass spectrometer. The column was a 30 m×0.25 mm Rtx-65TG with a 0.1 µm film. The column oven was initially held at 40° C. for 5 minutes and then programmed in two stages: from 40 to 200° C. at 10° C./min and then from 200 to 350° C. at 20° C./min. The column is held at the final temperature for 11.5 minutes. Runs with both split and splitless injection were made.

Conditions for the GC analysis are provided in Table 3 below. All components were assumed to have the same response factor. Samples were dissolved in isooctane prior to analysis.

TABLE 3

| GC Method | |
|---|---|
| Parameter | Conditions |
| Column | 30 m × 0.25 mm Rtx-65TG with 0.1 µm film |

TABLE 3-continued

| GC Method | |
|---|---|
| Parameter | Conditions |
| Oven temperature program | 40° C. for 2 minutes, then 10° C./min to 350° C. |
| Flow rate | 4 mL/min, Constant flow |
| Carrier gas | Hydrogen |
| Injection volume | 1 µL |
| Injection mode | Split |
| Split ratio | 20:1 |
| Injector temperature | 300° C. |
| Detector temperature | 375° C. |
| Detector | Flame ionization |

GPC Analysis

GPC data were acquired on an Agilent 1260 system equipped with refractive index detector. We examined the isomerized C18 sample by GPC in order to confirm the presence of hydrocarbons intermediate in carbon number between 18 and 36. These data again indicated that the sample consists of a range of components with C18s present at the largest concentration and that higher carbon number components were present in the sample. The early eluting band at approximately 15 minutes was most likely due to C36 components. The components eluting between 15 and 16.8 minutes corresponded to the C19-C35 grouping in the GC.

1-octadecene was isomerized in the same conditions. The crude product from isomerization of 1-octadecene (1162-91) contains more dimers compare to C18 isoparaffins from 9-octadecene.

1-Octadecene isomerization might favor more dimer formation compare to 9-octadecene where the internal double bond might generate sterically hindered isomers that will not further dimerize. GPC method conditions are set forth in Table 4.

TABLE 4

| GPC Method | |
|---|---|
| Parameter | Conditions |
| Column | Set of 2 OligoPore columns 300 × 7.5 mm |
| Column oven temperature | 40° C. |
| Flow rate | 1 mL/min |
| Mobile phase | THF, stabilized with BHT |
| Injection volume | 20 µL |
| Detector | Refractive Index |

Physical Property Comparisons

The physical properties (viscosity, refractive index, TGA volatility, spreadability, pour point, lubricity (friction coefficient), and compatability with other ingredients) of the isoparaffins and mixtures were evaluated and compared to D5 and isohexadecane.

The increase of branching had a significantly effect on the pour point. A fully isomerized C18 pour point is −51° C., compare to partially isomerized C18 with a pour point of 12° C. and a linear chain C18 solid at 25° C.

C18 isoparaffin mixture is compatible/miscible with polar, nonpolar and silicone based cosmetic ingredients at any concentration (tested at 10% and 25%). Table 5 shows the properties of the isoparaffins of the invention in comparison to silicone D5 material and isohexadecane.

TABLE 5

| Sample | D5 | Iso-hexadecane | C18 isoparaffins pure | C18 isoparaffins w/dimer | C18 partially isomerized | C18 isoparaffins 1-octadecene |
|---|---|---|---|---|---|---|
| Appearance at RT | Clear Liquid, colorless | Clear Liquid, colorless | Clear Liquid, colorless | Clear Liquid, colorless | Clear Liquid, colorless | Clear Liquid, colorless |
| viscosity at 25° C., cPs | 5.5 | 4.1 | 4.44 | 6.96 | 4.8 | 8.05 |
| refractive index | 1.4001 | 1.4434 | 1.4443 | 1.4497 | 1.4439 | 1.4494 |
| surface tension, mN/m 20 C. | 17.93 | 24.02 | 26.77 | 26.91 | TBD | TBD |
| pour point |  |  | −51 | −42 | 12 | −30 |

Spreading Characteristics

To test the spreading characteristics, a method described in WIPO patent application WO2010019939A1 was used. 110 mm Whatman #4 filter paper was positioned horizontally over an open jar. Fifty microliters of product were then transferred via a syringe onto the center of the filter paper. The spreading area of the liquid was then measured at intervals of one, three, and five minutes. The spreading rate and viscosity are properties of an emollient that contribute to skinfeel or tactile impression. Rapidly spreading/low viscosity products are perceived as "light", whereas slow spreading/higher viscosity products are perceived as "heavy." Table 6 shows these spreading characteristics below.

TABLE 6

| time | C18 iso-paraffins with dimer | D5 | C18 iso-paraffins, no dimers | Partially isomerized C18 | C18 iso-paraffins from 1-octa-decene | iso-hexa-decane |
|---|---|---|---|---|---|---|
| 1 min | 38 | 36 | 40 | 38 | 33 | 41 |
| 3 min | 47 | 44 | 50 | 47 | 42 | 49 |
| 5 min | 50 | 48 | 54 | 52 | 48 | 53 |

The spreading properties in this test of C18 isoparaffins were comparable to isohexadecane and better than D5. Note: 5 minutes is shown at the top of a given composition, 3 minutes in the middle, and 1 minute at the bottom.

Coefficient of Friction Testing

Coefficient of friction of neat materials was evaluated using the Mini Traction Machine (MTM) and an internal method. The measurements were taken at controlled temperature and humidity. Conditions of the test were designed to mimic realistic personal care product application scenarios, as set forth in: Fourtoni et al., Tribology Int'l, vol. 40, pp. 1531-1542 (2007); Littich et al., Household & Personal Care Today, vol. 9, pp. 18-20 (2014). The results are highlighted below.

Friction is a major factor when the skin care or hair care product is applied. Friction is the resistance of two contacting surfaces to relative motion. It is proportional to normal force and the proportionality constant is defined as the coefficient of friction.

A decrease in coefficient of friction indicates slipperiness which translates to better lubricity and feel (good rub-in characteristics, drag reduction). For hair care products that translates to a decrease in hair friction, less hair tangling and minimizing the combing force.

The invention claimed is:

1. A method of forming an isoparaffin composition, the method comprising:
   providing (a) unsaturated alkyl esters and (b) low-molecular-weight olefins;
   reacting the unsaturated alkyl esters and the low-molecular-weight olefins in the presence of a metathesis catalyst to form a metathesis product comprising metathesized esters and metathesized olefins, wherein the metathesized olefins comprise one or more linear internal olefins;
   separating at least a portion of the metathesized olefins from the metathesis product to form a separated olefin composition, wherein the separated olefin composition comprises one or more linear internal olefins;
   isomerizing the one or more linear internal olefins comprised by the separated separated olefin composition to form a isomerized olefin composition, wherein the isomerized olefin composition comprises one or more branched olefins; and
   hydrogenating the one or more branched olefins comprised by the isomerized olefin composition to form an isoparaffin composition.

2. The method of claim 1, wherein the unsaturated alkyl esters comprise esters derived from natural oils.

3. The method of claim 1, wherein the unsaturated alkyl esters comprise polyol esters of alkenoic acids.

4. The method of claim 3, wherein the unsaturated alkyl esters comprise glycerol esters of alkenoic acid esters.

5. The method of claim 1, wherein the unsaturated alkyl esters comprise alkyl esters of alkenoic acids.

6. The method of claim 5, wherein the unsaturated alkyl esters comprise methyl esters of alkenoic acid esters.

7. The method of claim 1, wherein the low-molecular-weight olefins comprise $C_2$-$C_{18}$ olefins.

8. The method of claim 1, wherein the metathesized olefins comprise 9-octadecene.

9. The method of claim 1, wherein the separated olefin product comprises 9-octadecene.

10. The method of claim 1, wherein the isomerizing is carried out in the presence of a zeolite.

11. The method of claim 1, wherein the isoparaffin composition comprises no more than 5 weight percent C36 alkanes, based on the total weight of alkanes in the isoparaffin composition.

* * * * *